US011195271B2

(12) United States Patent
Chauhan

(10) Patent No.: US 11,195,271 B2
(45) Date of Patent: Dec. 7, 2021

(54) CONFIDENCE-BASED METHOD AND SYSTEM FOR ANALYZING IMAGES OF A RETINA

(71) Applicant: Macuject Pty Ltd, Kew (AU)

(72) Inventor: Devinder Singh Chauhan, Kew (AU)

(73) Assignee: Macuject Pty Ltd.

( * ) Notice: Subject to any disclaimer, the term of this patent is extended or adjusted under 35 U.S.C. 154(b) by 55 days.

(21) Appl. No.: 16/416,595

(22) Filed: May 20, 2019

(65) Prior Publication Data
US 2020/0372632 A1 Nov. 26, 2020

(51) Int. Cl.
*G06T 7/00* (2017.01)
*A61B 3/00* (2006.01)
*G06T 7/11* (2017.01)

(52) U.S. Cl.
CPC .......... *G06T 7/0012* (2013.01); *A61B 3/0025* (2013.01); *G06T 7/11* (2017.01); *G06T 2207/10101* (2013.01); *G06T 2207/20081* (2013.01); *G06T 2207/30041* (2013.01)

(58) Field of Classification Search
CPC ........ A61B 3/0025; G06T 2207/10101; G06T 2207/20081; G06T 2207/20084; G06T 2207/30041; G06T 7/0012; G06T 7/11
See application file for complete search history.

(56) References Cited

U.S. PATENT DOCUMENTS

| 2015/0062590 A1 | 3/2015 | Bagherinia |
| 2017/0119242 A1 | 5/2017 | Jia et al. |
| 2018/0047159 A1 | 2/2018 | Schlegl et al. |
| 2018/0132725 A1 | 5/2018 | Vogl et al. |

FOREIGN PATENT DOCUMENTS

EP  3065086 A1  9/2016

OTHER PUBLICATIONS

Chen, et al., Automated Drusen Segmentation and Quantification in SD-OCT Images, Dec. 2013, vol. 17, No. 8, pp. 1058-1072.
Venhuizen, F. G et al., "Deep learning approach for the detection and quantification of intraretinal cystoid fluid in multivendor optical coherence tomography", Biomedical optics express, vol. 9, No. 4, published Apr. 1, 2018, pp. 1545-1569 <URL: https://www.ncbi.nlm.nih.gov/pmc/articles/PMC5905905/pdf/boe-9-4-1545.pdf>.

(Continued)

*Primary Examiner* — Manuchehr Rahmjoo
(74) *Attorney, Agent, or Firm* — McAndrews, Held & Malloy, Ltd.

(57) ABSTRACT

Methods and systems of analyzing images of a retina captured by an Optical Coherence Tomography (OCT) scanner are disclosed. The methods and systems use a processor configured to implement a series of instructions that include creating a training set of images of a retina of a patient captured by an OCT scanner including labeled regions of diffuse intraretinal fluid (DIRF) such as by assessing maximum and minimum regions of DIRF and regions of pathology of the retina to generate a model, and analyzing the DIRF region or regions of pathology by the model to derive an assessment of the retina of the patient. The assessment of the retina enables, for instance, the treatment of the patient's retina to be evaluated and determined.

7 Claims, 12 Drawing Sheets

(56) References Cited

OTHER PUBLICATIONS

Vidal, P. L et al., "Intraretinal fluid identification via enhanced maps using optical coherence tomography images", Biomedical Optics Express, vol. 9, No. 10, published Oct. 1, 2018, pp. 4730-4754 <URL: https://www.ncbi.nlm.nih.gov/pmc/articles/PMC6179401/pdf/boe-9-10-4730.pdf>.

Schmidt-Erfurth, U. et al., "A view of the current and future role of optical coherence tomography in the management of age-related macular degeneration", Eye (2017) 31, Macmillan Publishers Limited, published online Nov. 25, 2016, pp. 26-44 <URL: https://optima.meduniwien.ac.at/fileadmin/PublicationPDFs/2016_schmidterfurt_review_eye2016227a.pdf>.

International Search Report, PCT/IB2020/000357, dated Jul. 31, 2020.

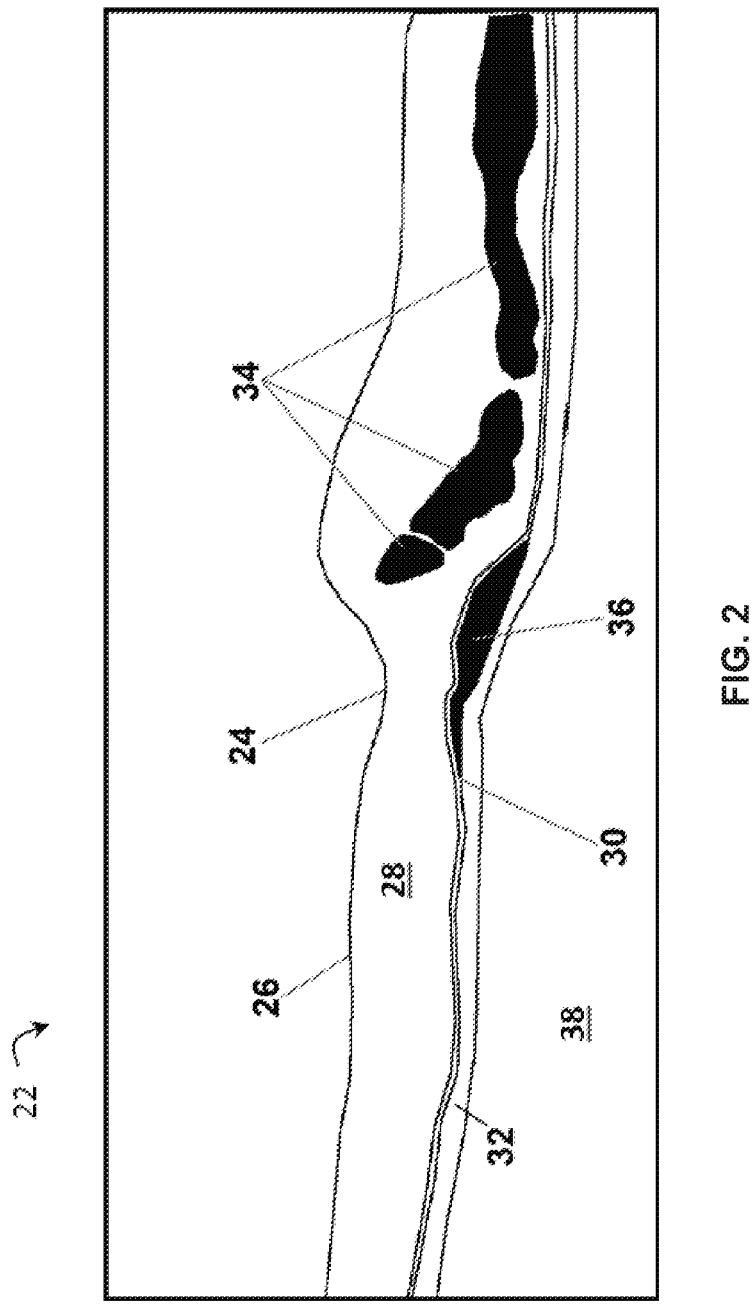

CONFIDENCE-BASED METHOD AND SYSTEM FOR ANALYZING IMAGES OF A RETINA

TECHNICAL FIELD

The present disclosure relates to methods and systems of analyzing images of a retina captured by an Optical Coherence Tomography (OCT) scanner. In particular, but not exclusively, the methods and systems use a processor configured to implement a series of instructions that include receiving images of a retina of a patient captured by an OCT scanner, determining regions of diffuse intraretinal fluid (DIRF) including by probability labelling and/or assessing maximum and minimum regions of DIRF and regions of pathology of the retina, and analyzing the DIRF region or regions of pathology to derive an assessment of the retina of the patient. The assessment of the retina enables, for instance, the treatment of the patient's retina to be evaluated and determined.

BACKGROUND

The inner coats of the human eye are responsible for vision. Working from the outside inwards, these coats include: the choroid; the retinal pigment epithelium; and the retina itself. Diseases affecting these and adjoining coats can have a significant effect on vision. The choroid is comprised of a dense plexus of blood vessels, which supply oxygen and nutrients to the outer retina and retinal pigment epithelium. The inner aspect of the retina is also vascularized; these retinal blood vessels supply the inner aspect of the retina.

Many diseases affecting the eye, particularly those with a vascular component to their pathology, cause disruption of the retina and choroid, with resultant visual effects. These diseases may be primarily ocular or systemic. Examples of these include age-related macular degeneration (AMD), diabetic retinopathy and retinal vein occlusion.

The integrity of the blood vessel walls and the flow within the blood vessels govern the mechanisms by which diseases affecting blood vessels cause harm to vision. Reduced or absent blood flow in the retina may result in retinal and anterior segment neovascularization, such as in diabetic eye disease. Damage to retinal blood vessel walls can also result in hemorrhage within the retina and ischemia; examples include retinal vein occlusion and diabetic eye disease.

The most commonly treated conditions affecting the macula, however, relate to leaky blood vessels. That is, damage or immaturity of retinal or choroidal blood vessel walls results in a net outflow of fluid from a capillary bed. Any disruption to blood vessel walls, particularly to the components of the blood retinal barrier, can result in a net outflow of fluid from capillary beds into tissues. This leads to the development of a swelling of the retina and is commonly seen as macular edema. Macular edema can be either symptomatic or asymptomatic; the presence and degree of symptoms depends on a number of factors. These include the location and extent of the macular edema, as well as its effect on intracellular and extracellular matrix, particularly with respect to metabolic and visual function.

The retina is not homogeneous, consisting of several well-described layers on histological sections. The layers of the retina may include: retinal pigment epithelium layer; photoreceptor layer of inner and outer segments; outer limiting membrane; outer nuclear layer; outer plexiform layer; inner nuclear layer; inner plexiform layer; ganglion cell layer; retinal nerve fiber layer; and inner limiting membrane. Whilst the anatomical layering of the retina appears to be orientated such that the layers are essentially organized concentrically in the eye and roughly parallel to the surface of the retina, the functional organization of the retina is orthogonal to this plane. That is, each of the histological layers is comprised primarily of a single cell or cell component type. However, there are multiple interconnections between layers, primarily synaptic, but also neuronal, glial or structural. The disruption of macular function (vision) by the presence of macular edema is probably due to both physical deformation/disruption and biochemical effects on individual cells, the retinal layers and their interconnections.

The fovea is the central part of the macula, with the highest concentration of photoreceptors. Disease affecting the center of the fovea generally has a greater impact on visual function. As discussed in Australian Application No. 2018903511, filed on Sep. 18, 2018, pathological changes in the shape and topology of individual layers of the retina, or clinically relevant combinations of layers, and the relationship of these to the location and shape of the fovea are likely to be of relevance to both treatment decisions and prediction of treatment outcome.

The constituents of the fluid that leaks from blood vessels include water, protein, lipids, and sometimes platelets and red and white blood cells. In addition, differential leakage and reabsorption may result in possible concentration or dilution of leaked blood constituents. It is believed that extracellular fluid diffuses and spreads within the retina within retinal layers as well as extending into neighboring layers. This distribution is likely to be influenced partly by the orientation of structural components within the retina as well as mechanical, extracellular and intercellular barriers to free flow of fluid. As a consequence of these constraints, there is deformation and disruption of the topology and thickness of individual layers of the retina and choroid, as well as their boundaries and interfaces. The location and extent of these changes influences vision both in the short and long term.

The regions of pathology include both focal regions of pathology and non-focal regions of pathology and may include subretinal fluid (SRF), focal intraretinal fluid (FIRF), diffuse intraretinal (DIRF), drusen, reticular pseudodrusen, subretinal hyper-reflective material intraretinal hyper-reflective foci, geographic atrophy; retinal pigment epithelial detachments, atrophic cysts, photoreceptor disruption/space, and outer retinal tubulation.

On an histological basis, macular edema can be seen as either a diffuse thickening of the whole macula, layers within it, or cystoid spaces. The latter may be simply collections of fluid, whereas the surrounding areas of diffuse thickening include areas of cellular abnormality and extracellular interstitial fluid that has not coalesced or saturated to form a cystoid space. It is likely that diffuse macular edema surrounds cystoid spaces and is an earlier sign of vascular leakage. Indeed, diffuse macular edema is likely to be a more sensitive and specific sign of leakage, cystoid spaces only being present once the leakage has exceeded the threshold for pooling of extracellular fluid or if there has been structural collapse. The development of diffuse macular edema often precedes cystoid macular edema. It is important, therefore, to distinguish between diffuse intraretinal fluid (DIRF) and focal, or cystoid, intraretinal fluid (FIRF). DIRF may be understood as a subtle swelling of the retina that occurs before, remains after and exists around focal (or cystic) intraretinal fluid changes in exudative macular diseases, which are due to leakage of fluid from pathological retinal and/or choroidal blood vessels into and/or under the macula. For example, DIRF may occur prior to the formation of focal, or cystic, intraretinal fluid (FIRF) and persist after resolution of FIRF. Functionally, the nature of the deformation and disturbance of tissues within layers of the macula may be of significance. That is, the relative location, juxtaposition and other relationships between regions of DIRF and FIRF may have a correlation with visual function and be of prognostic value.

From a clinical perspective, identifying and/or measuring the extent and severity of DIRF is valuable for diagnosing and treating macular disease, as the extent and rate of development of the pathology has implications for its prognosis and treatment.

Optical coherence tomography (OCT) is a non-invasive imaging technique used to generate three-dimensional cross-sectional scans of retina and other tissues. Spectral domain and swept source OCT are now of significantly higher resolution than previous iterations of OCT. It is therefore possible to readily recognize, segment and measure individual layers and combinations thereof using this technology. In spite of this, OCT images are not the same as histologic cross sections. Whilst there is a strong correlation between histological and OCT images, the latter are generated as a result of the optical perturbations of the incident light on a tissue, rather than simply its cellular constitution and organization; the optical properties of superficial layers influence the imaging of deeper layers. In use, an OCT scanner generates a set of A-scans across a retina to generate a cross-sectional reconstruction of the retina known as a B-scan. B-scans are cross-sectional reconstructions of the retina and adjacent B-scans are reconstructed or lined-up in order to produce a three-dimensional scan, sometimes known as a macular cube.

The intensity of OCT signals relates to many optical properties of the tissue; interfaces between layers of different refractive indices, the optical density and backscattering properties of individual cells, their organelles and their organization within layers of the retina all influence signal intensity and the intensity of signal from deeper tissues. It has been established that bodies of clear serous fluid generate a low signal. In an example of existing OCT scans of the macula of an eye, a focal region of pathology in the form of focal intraretinal fluid (FIRF) can be seen as distinct and discrete dark spaces that are readily identified on inspection by most observers and have been detected, delineated and labeled by several automated and artificial intelligence (AI) programs. Diffuse intraretinal fluid (DIRF), however, has been, by contrast, difficult to reliably identify and label, both by expert image graders (e.g., a clinician) and/or AI software. Also, quantification of DIRF has not been achieved reliably enough to inform clinical decision-making with respect to assessment for treatment for, say, macular edema. That is, existing segmentation techniques, to determine regions of pathology of the retina, such as DIRF, may have too low accuracy or may be too unreliable to be used to clinically assess the retina of a patient.

Clinicians have identified and/or measured DIRF by manually labelling or annotating a retinal image of an OCT scan. The boundary of a region of DIRF and/or FIRF is thus determined by visual inspection by the clinician, which is prone to visual limitations and subjective analysis of the labeler. Annotated data for DIRF are necessarily imprecise, as different raters perceive the presence of DIRF differently, there being no obvious boundary on inspection. Therefore, inconsistencies occur when different clinician labelers annotate the same image, even when the labelers are very experienced. Automated software techniques generally indicate merely the presence or absence of fluid (namely DIRF) without providing reliable information about its location or any measurements related thereto.

Moreover, current systems are deficient in that, while they are relatively adept at identifying FIRF, as discussed above, detecting DIRF has proven challenging for conventional application as the regions of the retina associated with the DIRF are not as clearly and discretely hyporeflective as are regions associated with FIRF. For example, the only apparent changes between an imaged region of DIRF and an imaged region of FIRF may be a subtle reduction of the OCT signal in the affected area (e.g., a change in relative brightness) and/or a swelling or distortion of retinal layers in the region around the affected area. Furthermore, DIRF may not have a single consistent presentation in an OCT image. For instance, the degree of fluid accumulation (and hence the extent of reflectivity change on the OCT image) may be variable even within a contiguous affected region and/or on different images of a single scan.

Some methods and systems of addressing these issues of accuracy and reliability are addressed in Australian Application No. 2018903511 filed on Sep. 18, 2018, which is hereby incorporated by reference. However, a need exists for additional reliable and accurate systems and methods for locating and analyzing retinal fluid consistently and reliably and treatment methods based on these systems and methods. The present invention may be used with or separately from the invention described in the aforementioned Australian application.

The above discussion of background art is included to explain the context of the present invention. It is not to be taken as an admission that any of the documents or other material referred to was published, known or part of the common general knowledge at the priority date of any one of the claims of this specification.

SUMMARY OF INVENTION

Aspects of the present application includes methods and systems of analyzing images of a retina captured by an Optical Coherence Tomography (OCT) scanner.

In one aspect, the system includes at least one OCT image of a retina obtained from a patient. A memory includes a trained model configured to determine the location of diffuse intraretinal fluid (DIRF) in the retina based upon the at least one OCT image. The model is configured to determine the location of fluid based on different OCT images in a training set, and the different OCT images of the training set comprise a plurality of images that each comprise at least two labels that distinguish between high and low confidence locations of fluid. A display outputs the location of the fluid in the patient retina.

In some embodiments, the model may be trained via machine learning. The system may further include an optical coherence tomography scanner configured to acquire OCT images. The model may be further configured to determine the volume of retinal fluid and the display outputs the volume of the fluid. The display output may be a fluid confidence map. The trained model may be further configured to determine the location of focal intraretinal fluid (FIRF) in the retina.

In some embodiments, a method of creating a model for analyzing images of a retina captured by an optical coherence tomography (OCT) scanner is disclosed. The method includes acquiring a plurality of OCT retinal images; labelling each of the OCT images with a first and second label wherein the first label reflects a relatively high probability of the location of diffuse intraretinal fluid (DIRF) in an OCT image and the second label reflects a lower probability of the location of DIRF in the OCT image; creating a training set of OCT images that comprises the labelled OCT images; introducing the labelled images to a processor for training; and training a neural network on the training set such that the training outputs a model configured to determine the location of DIRF in unlabeled OCT images.

In one aspect, the method may further include the step of validating the model. The first label may reflect a minimum DIRF region and the second label reflects a maximum DIRF region. The first and second labels may represent a boundary between estimated regions of fluid and no fluid where the first label reflects a high confidence level in the boundary and the second label reflects a low confidence level in the boundary. The method may include more than first and second labels and the additional labels reflect different degrees of confidence in the probability of fluid at a given location of an OCT scan in the training set. The method may further include aggregating first and second labels of a single OCT image from more than one labeler. In some embodiments, a system includes a memory which includes the disclosed model.

In one aspect, a method of treating a patient for macular disease is disclosed. In some embodiments, the method includes obtaining at least one OCT image of a retina from a patient; inputting the OCT image into a processor on a system with a memory comprising a trained model configured to determine the location of diffuse intraretinal fluid (DIRF) in the retina wherein the model is trained to determine the location of fluid based on OCT images that include at least two labels that distinguish between high and low confidence locations of fluid; and assessing a display that outputs the location of the fluid in the patient retina based on the trained model.

The method of treating a patient may further include prescribing a treatment plan after using the model to compare the volume of fluid in a first patient OCT image to the volume of fluid in second patient OCT image from the same eye of the same patient. In some embodiments, the method may include receiving an image of a retina of a patient captured by an OCT scanner; determining regions of diffuse intraretinal fluid (DIRF) in the image using a trained model that is configured to analyze the location of diffuse intraretinal fluid on an OCT scan based on high and low confidence labels of said fluid in a training set; and outputting an image of predicted location of intraretinal fluid based on the trained model.

In some embodiments, a system for analyzing images of a retina includes an Optical Coherence Tomography (OCT) scanner configured to capture images of a retina, each of the images having a plurality of pixels. A memory includes a series of instructions in the form of a trained model that is configured to analyze the location of diffuse intraretinal fluid (DIRF) on images received from the OCT scanner based on probability-based labels relating to the level of DIRF in a training set. A processor is in data communication with the OCT scanner and the memory that is configured to implement the series of instructions that include receiving an image of a retina of a patient captured by the OCT scanner, determining regions of DIRF in the image including by assessing the relative probabilities of DIRF at a given location, and analyzing the DIRF region or regions of pathology to derive an assessment of the retina of the patient, and a display for outputting a fluid confidence map that reflects the location of intraretinal fluid as determined by the trained model.

Another aspect of one embodiment of the present invention includes software for use with a computer including a processor and memory for storing the software, the software including a series of instructions executable by the processor to carry out the methods claimed herein.

Another aspect of one embodiment of the present invention includes storing the image of the retina of the patient in a memory, receiving a subsequent image of the retina of the patient, and storing the subsequent image of the retina of the patient in the memory. Further, the assessment is also stored in a memory, and the method includes comparing the assessment with a subsequent assessment of the subsequent image of the retina of the patient to derive a progress assessment for the patient.

BRIEF DESCRIPTION OF THE DRAWINGS

Examples of the invention will now be described with reference to the accompanying drawings. It is to be understood that the examples are given by way of illustration only and the invention is not limited by this illustration.

FIG. 2 is a representation of an image of a retina captured by an OCT scanner.

DETAILED DESCRIPTION

Disclosed are systems and methods for detecting diffuse intraretinal fluid (DIRF) based on evaluation of images of an OCT scan of a patient's eye via one or more artificial intelligence (AI) techniques and that may in part rely upon the subjectivity in labelling to train a network to better identify DIRF. Generally speaking, and as described further herein, methods and systems include creating a training set of OCT scans by obtaining and labelling OCT scans, analyzing the OCT scans to assess retinal fluid (both focal and diffuse) including based on a confidence level of a fluid density and image brightness, assessing both maximum and minimum boundaries for DIRF or the level of confidence or probability that DIRF exists in certain locations (probability-based labeling), and assessing the scan in view of the labeled images including aggregation as necessary; training the network based on the training set; and using the trained system to reliably and consistently identify retinal fluid in new OCT scans including by outputting an image that depicts location of DIRF and also accounting for FIRF. Patient management by the clinician proceeds thereafter.

Methods and systems identify DIRF and/or FIRF via analysis of image characteristics such as over a broad and/or continuous spectrum of image brightness (e.g., on a pixel-by-pixel basis) and identify regions of localized fluid in the retina and/or may assess or quantify its volume, density and/or distribution. As disclosed with respect to the several figures, a processor executes a series of instructions, such as stored as code, to receive a plurality of annotated images (i.e. a common image annotated by a plurality of labelers, and/or multiple images labeled by one or more labelers) to generate a model to identify and/or quantify regions of DIRF and/or FIRF in an image of an OCT scan. For example, the model is trained on the annotated images by identifying inconsistencies in labels between graders to develop tools designed to identify and/or quantify the extent of DIRF in an OCT scan on a per-pixel basis.

Figure 1:
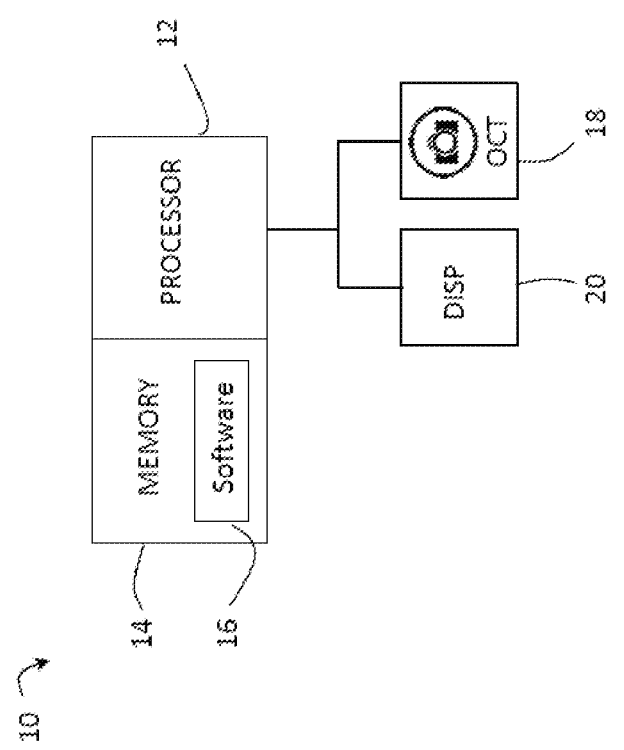
FIG. 1 is a schematic of a system for analyzing images of a retina.

A system 10 for analyzing images of a retina according to one example of the present invention is shown in FIG. 1. The system 10 includes a computer having a processor 12 and a memory 14. The memory 14 contains software 16, resident thereon, including computer code and/or a series of instructions executable by the processor 12 to configure the processor 12 to perform a number of steps to analyze images of a retina.

The system 10 may include an Optical Coherence Tomography (OCT) scanner 18 configured to capture the images of a retina, whereby each of the images has a plurality of pixels. The OCT scanner 18 may communicate with the processor 12 of the computer via a physical or wireless interface, or, in some examples, may form a single apparatus with the computer. In any case, the OCT scanner 18 is used for capturing images of a patient's retina.

It is noted that the location and volume of fluid (e.g., DIRF and/or FIRF) in disease (age-related macular degeneration, diabetic retinopathy and retinal vein occlusion) to be considered is also related to the position of the fovea. In order to describe and track changes in these features, the system 10 may implement steps for foveal finding and for image registration into a standard coordinate space.

Images of the retina may be stored in the memory 14 and/or on a remote server (not shown), and these images are accessible to the processor 12 for analysis. To do so, as described further herein, the processor 12 is configured by the software 16 to receive images including annotated images, determine regions of pathology of the retina including DIRF, and identify and classify characteristics within the images based on classification of the characteristics including as trained by the training set, and identify regions of fluid (e.g., DIRF and/or FIRF) and/or relative density of those regions in the image based on the analysis. The software is configured based on a training set of OCT scans. To create a training set of OCT scans, as discussed further herein, a processor 12 or another processor is configured by software to receive a training set of a plurality of OCT scans with corresponding labeled regions of both FIRF and maximum and minimum DIRF (and in some cases aggregate such annotated images), analyze the OCT scan for regions of DIRF and FIRF as further described herein, and output the location of the DIRF. The results of determinations of the regions of pathology are then used to generate a model, which can be used to derive an assessment of the retina of the patient. The assessment of the retina of the patient is then outputted to, for example, a display 20.

FIG. 2 shows a simplified B-scan image 22 from the OCT Scanner 18 of a macula of a retina of a patient. Here it can be seen that the retina has a fovea 24 located fairly centrally within the image 22 of the macula of the retina, and four layers defined by boundaries. The first boundary defines the surface of the macula 26. The first layer 28, beneath the surface 26, is a simplified representation of the whole of the neurosensory retina 28, the second layer is a representation of an outer surface of a neurosensory retina including a photoreceptor layer 30, and the third layer is the retina pigment epithelium layer 32. Beneath the retina pigment epithelium layer 32 is the choroid 38. The first layer 28 and the second layer 30 have regions of pathology located within and under, respectively. Specifically, the first layer 28 has intraretinal fluid 34 trapped within it. The second layer 30 also has subretinal fluid 36 trapped under it. The system 10 analyzing this image would, using the methods and systems described herein, determine locations of the intraretinal fluid 34 and subretinal fluid 36, and then use this to derive an assessment of the retina.

As disclosed herein, one or more characteristics of the regions may be used to derive the assessment. The properties include one or more of a relative density of fluid in the region, a two-dimensional size of the fluid region, the region shape, and/or a number of regions. In more specific embodiments of the present invention, the system 10 can be described as a pipeline for OCT image data processing and inferential modelling that operates in several stages. At a high level, the stages of the processing pipeline first include the steps associated with loading image data. Having developed a model through training on the annotated image(s), image data are produced by the OCT scanner 18 and are read into the data processing pipeline. Image data are created by an OCT scanner and transferred to a general purpose computer (with, e.g., a graphics processing unit, GPU), which is either contained in the same device as the OCT scanner or exists as a separate device on the same local network as the OCT scanner and/or remotely in a cloud computing environment. Image data may be represented as a binary file containing a single flattened array of pixel intensities. This array is reshaped into a cuboid which is indexable by coordinates in 3-dimensional space. The dimensions of the cuboid are dependent on the specific OCT scanner used to create the image, as well as the parameters of the scan performed.

In some examples, the classification of a characteristic corresponds to a level of fluid density in a region of the patient's eye corresponding to the location of the characteristic on the image. The various classes can be learned from training on annotated images from one or more labelers, as disclosed herein. The results of the identified and mapped regions of fluid (which may include the volume of the regions) are then used to derive an assessment of the retina of the patient. The assessment of the retina of the patient may then be outputted to a display 20.

The loaded images may be transformed in order to normalize for systematic differences in the images produced by different OCT scanners. OCT images captured by different OCT scanners have different characteristics in terms of their resolution, contrast, signal-to-noise ratio, etc. To improve compatibility with images generated by a range of different OCT scanners, a set of mechanisms for normalizing scans and making models robust to differences in the characteristics of different OCT scanner models are used. These methods include: normalizing scans with respect to contrast and scaling, performing data augmentation to vary the characteristics of training images, and fine-tuning machine learning models on a set of real training examples collected from the different OCT scanner models types.

The images are then registered to a common coordinate system so that the presence of a focal region of pathology, generally a fluid, at specific locations of the retina can be compared across scans taken from patients at different times and even across patients and OCT scanners. This preprocessing of images is used to standardize the appearance of images before the images are passed to the machine learning systems of the system 10.

As described herein, the system 10 may be used to derive an assessment of disease severity or response to treatment by for example, assessing image data associated with the retina, and then tracking the progression of the patient's disease including assessing the volume of fluid in any particular scan and comparing it with past patient scans. This may enable the system 10 to make predictions about the patient's future condition and about the best possible interventions based not only on the current features of the patient's disease but also on change over time such as by comparison of a patient's previous and current scans.

The features of disease (macular degeneration, diabetic retinopathy and retinal vein occlusion) to be considered are also related to the relative amount and location of DIRF. These features include the volume of fluid present and the shape, location and dimensions of DIRF. In order to describe and track changes in these features, the system 10 implements steps for ascertaining such changes.

Properties of the detected regions of pathology, including volume, size, signal characteristics and location, as well as changes from previous scans, are extracted from the images. The extracted features are then used to make determinations of and predictions about the patient's retina disease progression and optimal treatment choices.

Generally speaking, methods and systems disclosed herein implement a method and system for analyzing a retinal scan to determine location of retinal fluid and informing the treatment of macular disease in a patient if present. Methods and systems disclosed herein train an artificial intelligence tool (such as a neural network) to develop a model to identify location of DIRF in a retinal image scan. There are generally several aspects to the methods including as implemented by the systems. First, a training set of patient OCT scans are obtained and labeled (and in some cases aggregated) to identify both high confidence and low confidence areas of DIRF. Areas of FIRF may be identified according to known techniques described in the literature. The number of scans for the training set is variable but generally includes hundreds or thousands of OCT scans obtained for a large variety of different patients and may include normal and OCT scans with no fluid, some from patients with age-related macular degeneration. Using a system of high and low confidence labels as described herein, the network is then trained on the location of DIRF using the training set including via AI. The system may produce an image output for the training set that shows the location of the DIRF (and may also account for the FIRF) in any particular OCT scan. Preferably, the trained system is validated or otherwise evaluated to ensure confidence in the training. Once the network is trained, the system analyzes the location of DIRF in new OCT scans. The clinician uses the OCT scanner to obtain new scans from a patient and the scans are inputted into the system. The system analyzes the image and identifies the location of DIRF, outputting an image that shows the location of DIRF for the clinician. The system may also ascertain the volume of patient fluid based on the output and/or compare a current patient scan to past patient scan(s) to assess patient progress. The patient is thereafter treated by the clinician according to a program of treatment.

Figure 3A:
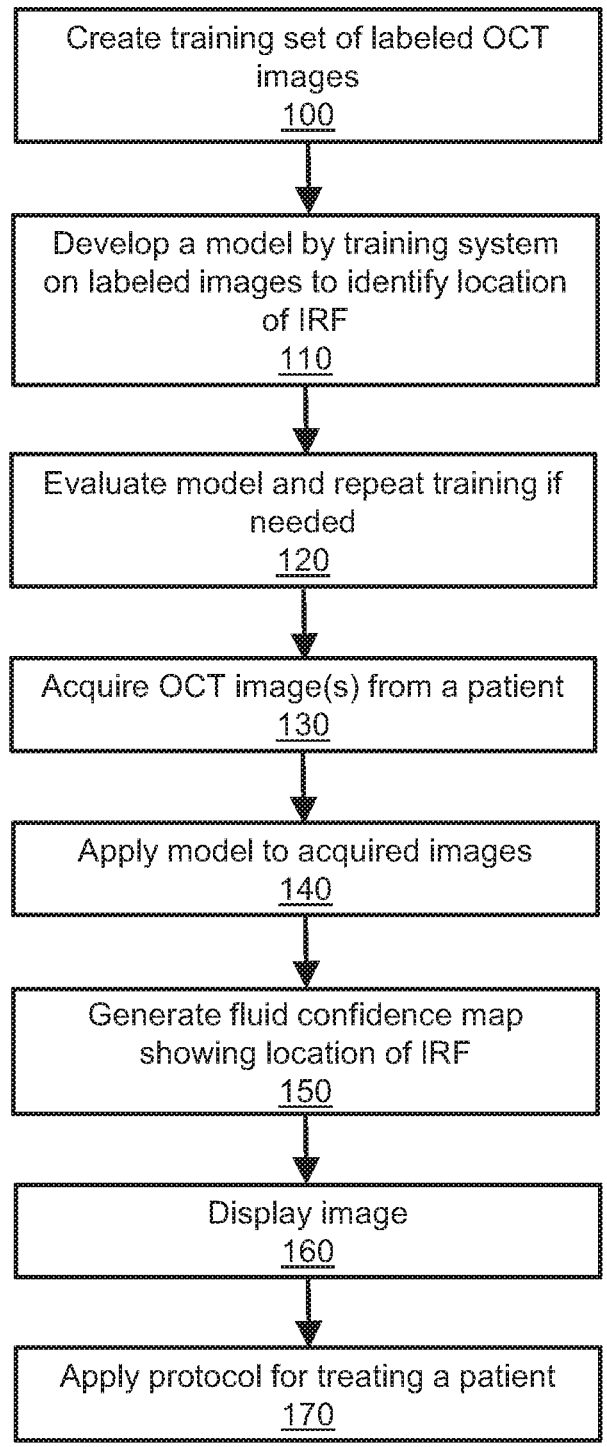
FIGS. 3A and 3B are flow charts summarizing a method of analyzing images of a retina and a method of creating a training set of labeled OCT images according to embodiments of the present invention.
Figure 3B:
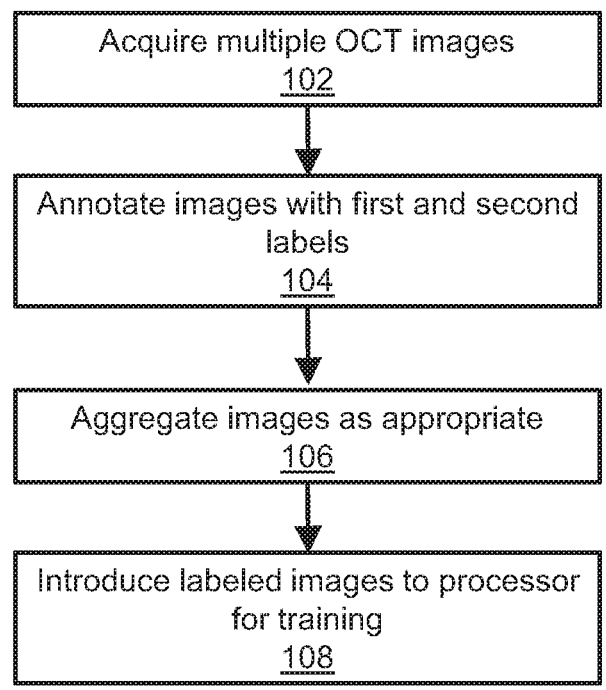

Referring now to FIG. 3A, there is shown a method of analyzing images of a retina captured by an Optical Coherence Tomography (OCT) scanner 18 including through use of a system. As disclosed herein, an artificial intelligence tool (e.g., as a neural network stored in software 16 or remote system) is applied to develop a model to identify regions of IRF, such as DIRF, in a retinal image scan. At block 100, a training set of labeled OCT images is created. A methodology for creation of the training set is shown in FIG. 3B. At block 110, a model is developed using a processor by training a network to identify locations of IRF (e.g., DIRF and/or FIRF) on the training set images. As disclosed herein, multiple annotations of images can be introduced to the system in order to train the neural network. The training results in a model configured to generate a fluid confidence map and identify location of retinal fluid including DIRF. The model may also calculate the volume of fluid to aid in clinician treatment and determine its location with respect to the fovea. Once the system is trained on the images, the model may be validated or evaluated for consistency and accuracy (with training repeated as necessary) as shown in block 120. In some examples, a level of confidence in the labeled images is generated and the evaluation can be repeated if a greater level of confidence is desired. The trained model is included in a system for evaluating or analyzing retinal images obtained by OCT.

Having developed a model with a desired level of confidence, an image or images of a retina are obtained from a patient via OCT retinal scan(s) (B-scans that may comprise a macular cube) in block 130. The OCT scanner 18 may be included in system 10 and may or may not be located remotely from the processor or memory. In block 140, the system applies the model included in the system 10, which may be located in memory 14, to acquired images obtained in block 130. For example, a new set of retinal scans can be acquired for analysis. In some examples, the images can be stored in memory 14 or in a remote storage device, and/or processed prior to analysis via processor 12 or other remote processor. In block 150, the model can generate an estimated fluid confidence map for the new set of images. The fluid confidence map can correspond to locations of IRF, such as DIRF, FIRF, or IRF (DIRF+FIRF), within the images. The model may calculate the amount of fluid in the fluid confidence map based on methodology known to a person of ordinary skill in the art. In block 160, an image is displayed depicting the location of IRF such as DIRF including for example on a display 20. At block 170, a clinician thereafter proceeds with a method of treating the patient if needed based on the output. The system may compare the current patient scan to prior scans to guide the clinician in treatment. After a model is trained, it is understood that OCT scan analysis may be repeated for a plurality of patients in which case, e.g., block 130, 140, 150, 160, and 170 are repeated for another patient using the same model created in blocks 100, 110, and 120.

Referring to FIG. 3B, the creation of the training set of labeled OCT images of block 100 may include acquiring multiple OCT images 102 and annotating or labeling the images with first and second labels 104. The labels may include both high and low confidence designations regarding location of retinal fluid on the acquired images. In some examples, labels corresponding to a FIRF area are analyzed and other labels may also be incorporated as discussed herein. As disclosed herein, the labels may be applied by a clinician via one or more marking tools, such as a human-machine interface and may be aggregated as shown in 106. The labelled images can be stored in memory, such as memory 14 and/or a remote storage device. The labeled images that form the training set are introduced to a processor for training the neural network in block 110. Other images may be included in the training set including images that contain no fluid and are not labelled. Moreover, it is understood that further training or learning reinforcement may be provided after a first set of images is provided for the initial training set allowing for a plurality of training sets.

In addition, it will be appreciated by those persons skilled in the art that further aspects of the method will be apparent from the above description of the system 10. Further, the persons skilled in the art will also appreciate that at least part of the method could be embodied in software (e.g. program code) that is implemented by the processor 12 configured to control the system for analyzing images of a retina. The software 16 could be supplied in a number of ways, for example of a tangible computer readable medium, such as a disc, or in the memory 14 as shown in FIG. 1.

A method of identifying a region of DIRF in a retinal image scan and treating a patient with retinal or other disease may begin with acquiring multiple images of an OCT retinal scan (i.e., B-scans) from a patient or patients to populate a training set. FIGS. 4A, 5A, 6A, 7A, 8A, 9A, 10A, and 11A depict examples of raw OCT scans that may be included in a training set. As discussed above, the training set may include hundreds or thousands of images. For the training set, an image that presents a region of DIRF and FIRF is labeled or annotated with at least two labels, generally by one or more clinicians. The labels may generally correspond to areas of relatively high and relatively low confidence that an identified region includes DIRF. The labeled images are introduced into a system for analysis by a processor as described further below. The system develops the model by receiving and analyzing labeled OCT image data as well as any other relevant image data including, e.g., OCT images with no fluid. The way in which the images are labeled affects the output produced by the trained model for new macular cube samples. The labelling may proceed in one of several ways in order to produce the appropriate model. More specifically, a plurality of expert labelers is tasked with labelling individual B-scans from a random sample of OCT macular cubes, and the labeling strategy includes one or more techniques. The images may correspond to a variety of diseases (e.g., as described herein) or no disease.

In one example, the training set includes images with probability-based labels, i.e., a label that reflects a relative probability that DIRF exists in a particular region. The annotated images of the training set include a first label corresponding to a minimum DIRF region, e.g., a region in which there is a relatively high level of confidence that the region includes DIRF. FIGS. 4E, 5E, 6E, 7E, 8E, 9E, 10E, and 11E depict annotated images of the first label depicting the minimum DIRF region of their respective OCT scan. The annotated images include a second label corresponding to a maximum DIRF region, e.g., a region in which there is a level of confidence that the region includes the boundary of the DIRF albeit with a low level of confidence). FIGS. 4D, 5D, 6D, 7D, 8D, 9D, 10D, and 11D depict the annotated images of the second label depicting the maximum DIRF region of their respective OCT scan.

In this and other examples, the labeler may be a clinician or one with training and expertise in interpreting OCT images of a retinal scan and identifying regions of DIRF, FIRF, and/or other characteristics of any eye within a retinal scan. Thus, when annotations and/or labelling are performed by a clinician, the labels are selected based on such training and expertise. As discussed further below, following annotation of the one or more images, the system is trained on the labeled images by analysis of the annotations of the maximum DIRF regions and the minimum DIRF regions or alternative high and low confidence regions. For instance, a maximum DIRF region corresponds to the clinician's best estimate as to the broadest extent of a DIRF region, whereas a minimum DIRF region corresponds to areas where the clinician is more certain of the boundaries of DIRF. Accordingly, the system anticipates a greater divergence of results between labelers with respect to the maximum DIRF region as this label is associated with a lower confidence level than the minimum DIRF region.

Figure 4F:
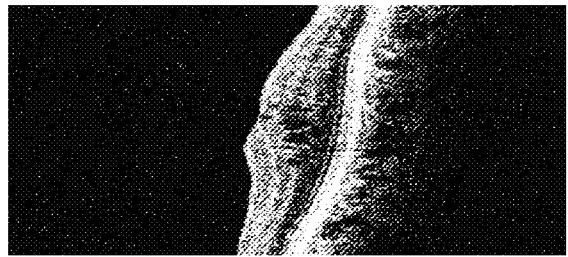
FIGS. 4A-4F, 5A-F, 6A-F, 7A-F, 8A-F, 9A-F, 10A-F, and 11A-F are illustrations of labeled and unlabeled OCT images as well as identification of retinal fluid including according to embodiments of the present invention. "A" labeled images (e.g., FIGS. 4A, 5A, 6A, 7A, 8A, 9A, 10A, and 11A) depict raw OCT images. "B" and "C" images depict outputs of DIRF and FIRF as identified by an embodiment of the present invention, respectively. "D" and "E" images depict maximum estimated extent of DIRF and minimum estimated extent of DIRF, respectively, as labeled by a retinal specialist. "F" images depict outputs of AI-labeled retinal fluid (FIRF and DIRF).
Figure 4E:
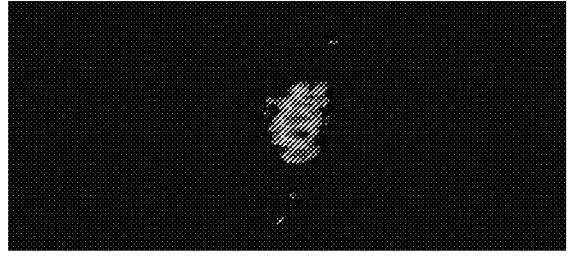
Figure 4D:
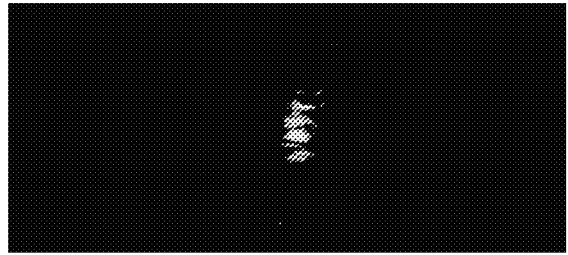
Figure 4C:
Figure 4B:
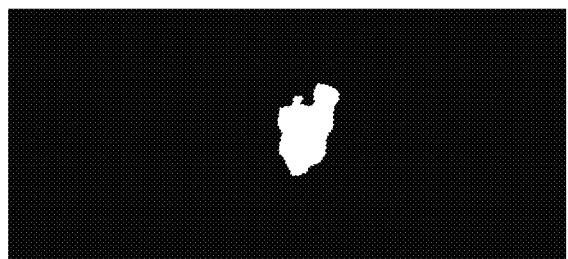
Figure 4A:
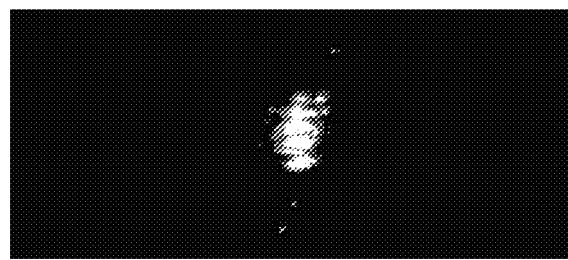
Figure 5F:
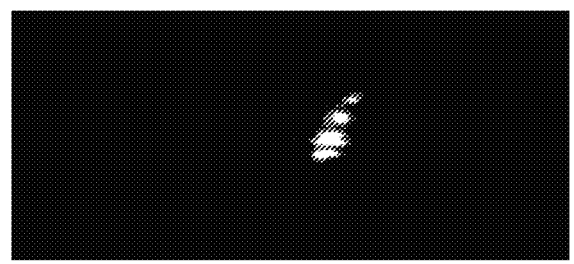
Figure 5E:
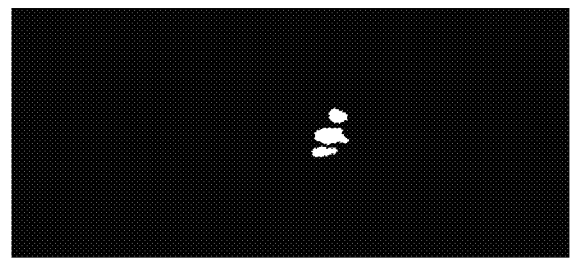
Figure 5D:
Figure 5C:
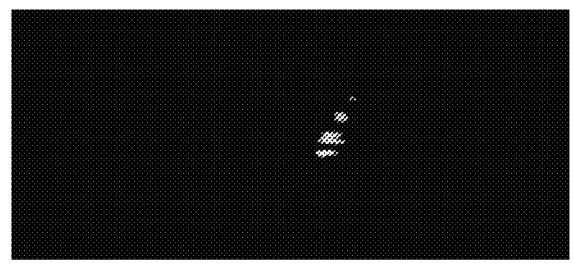
Figure 5B:
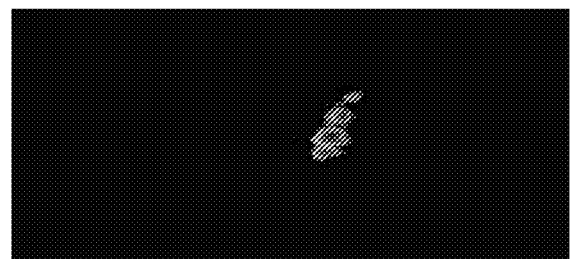
Figure 5A:
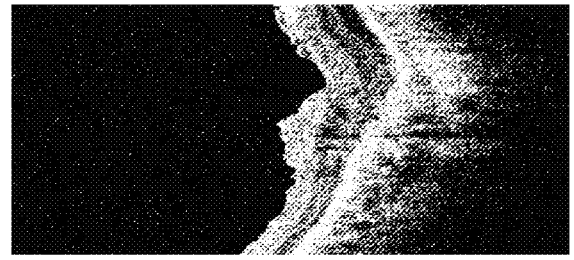
Figure 6F:
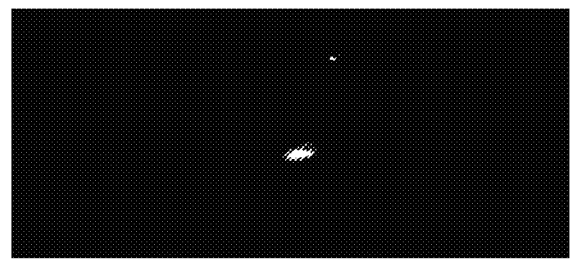
Figure 6E:
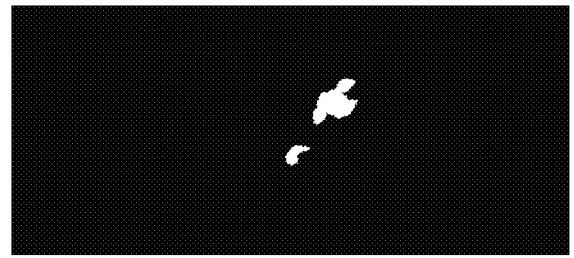
Figure 6D:
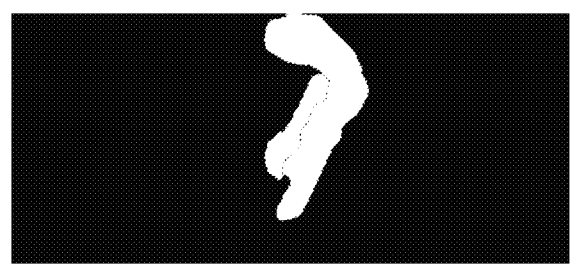
Figure 6C:
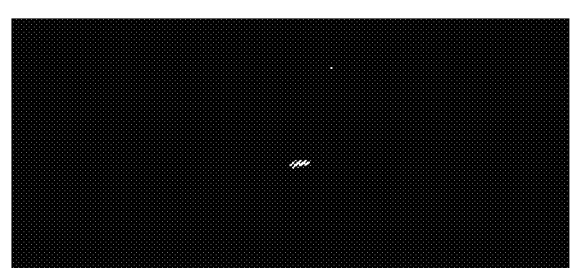
Figure 6B:
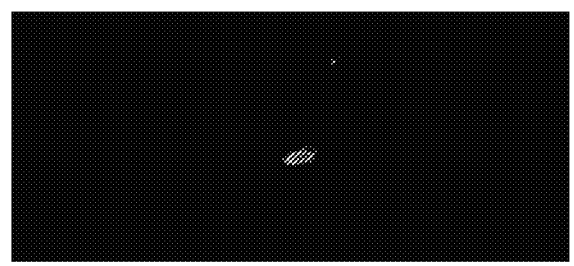
Figure 6A:
Figure 7F:
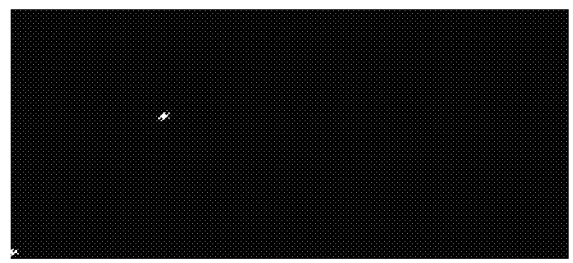
Figure 7E:
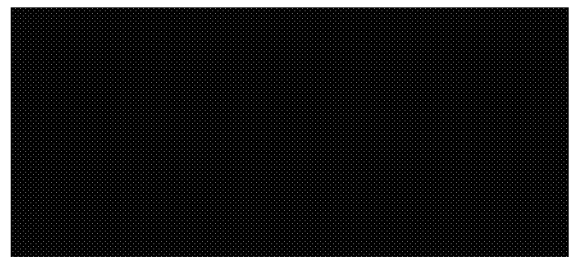
Figure 7D:
Figure 7C:
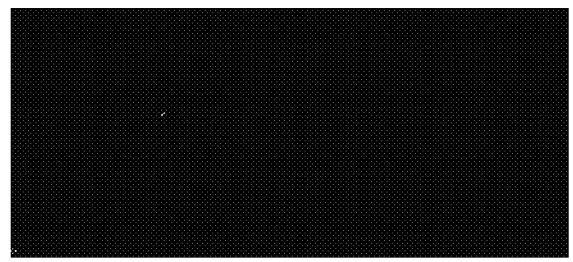
Figure 7B:
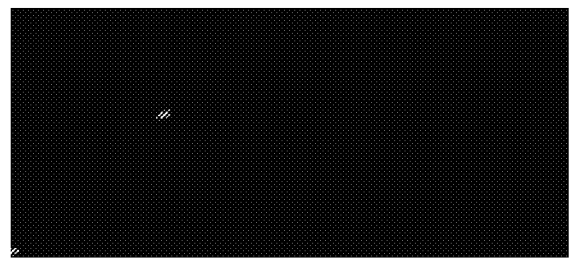
Figure 7A:
Figure 8A:
Figure 8B:
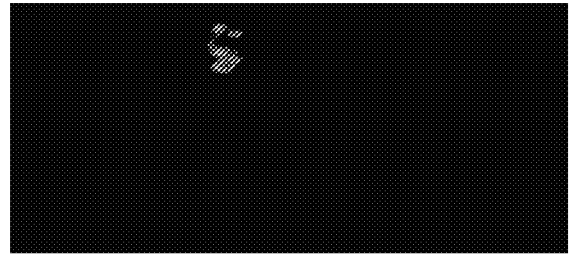
Figure 8C:
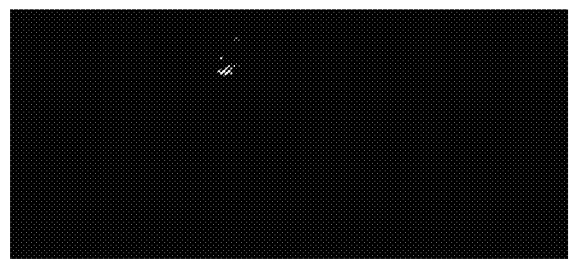
Figure 8D:
Figure 8E:
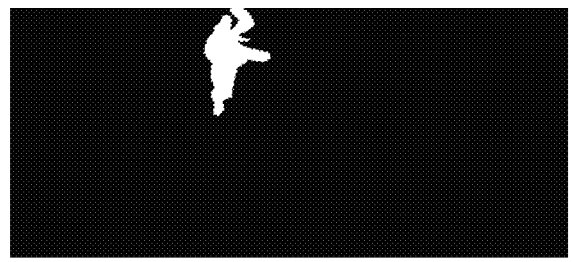
Figure 8F:
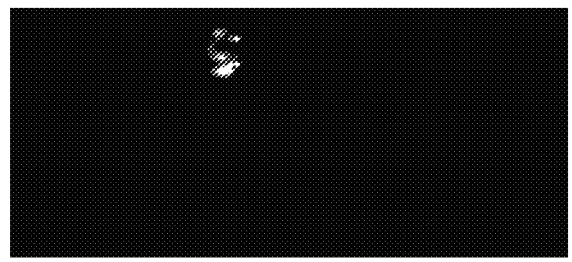
Figure 9F:
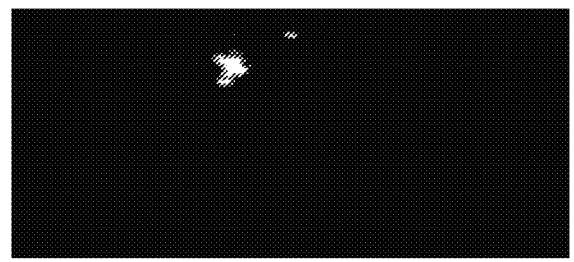
Figure 9E:
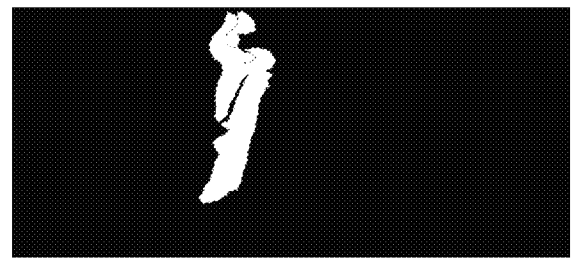
Figure 9D:
Figure 9C:
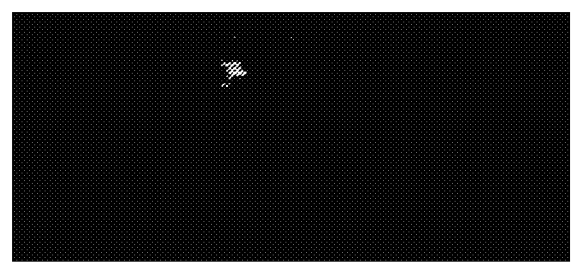
Figure 9B:
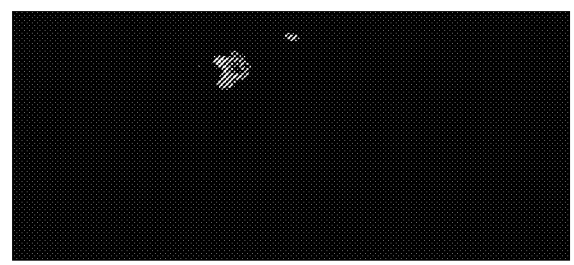
Figure 9A:
Figure 10F:
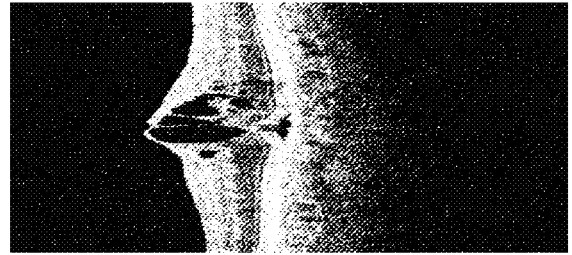
Figure 10E:
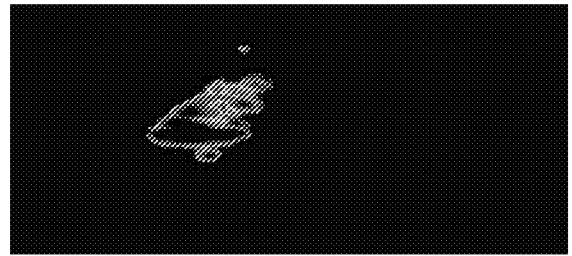
Figure 10D:
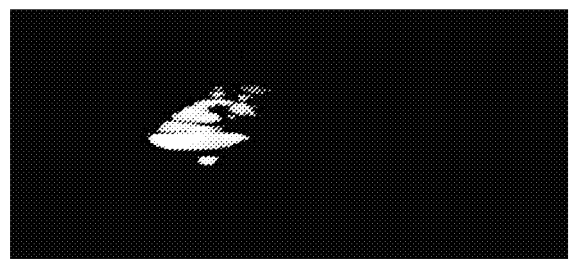
Figure 10C:
Figure 10B:
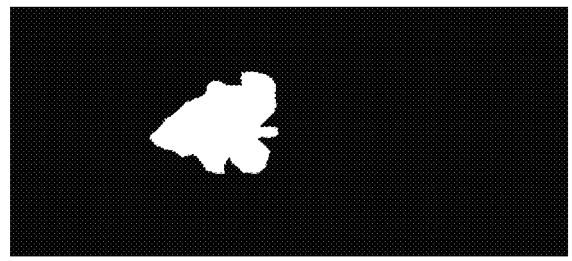
Figure 10A:
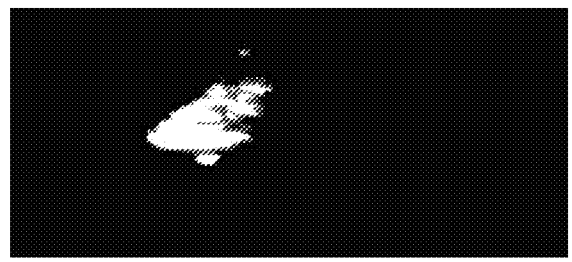
Figure 11A:
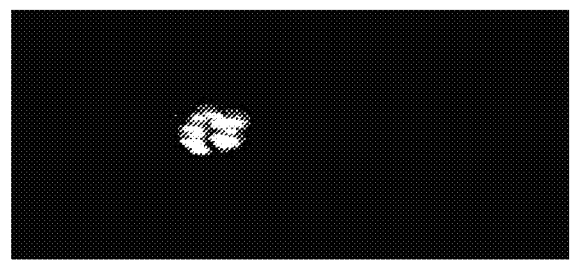
Figure 11B:
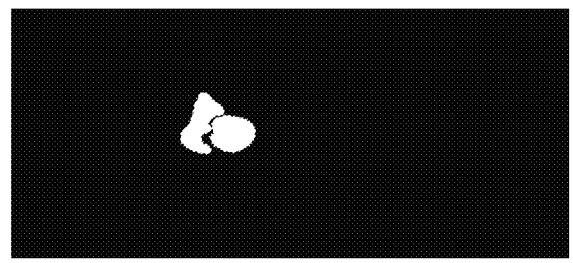
Figure 11C:
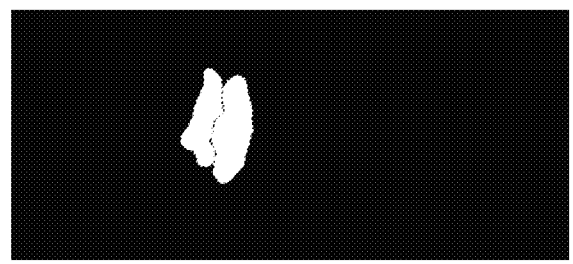
Figure 11D:
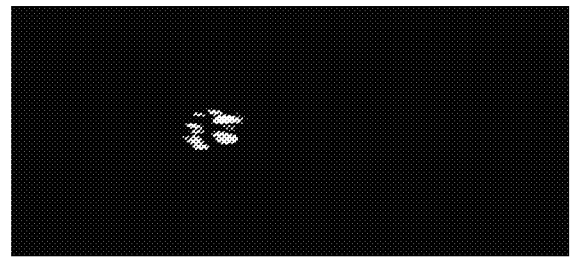
Figure 11E:
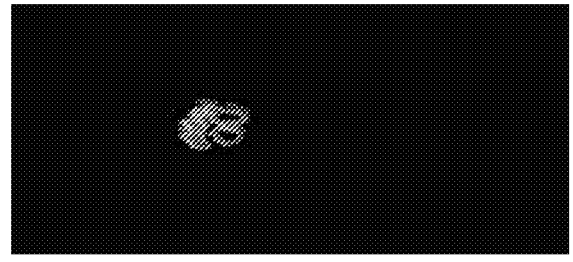
Figure 11F:
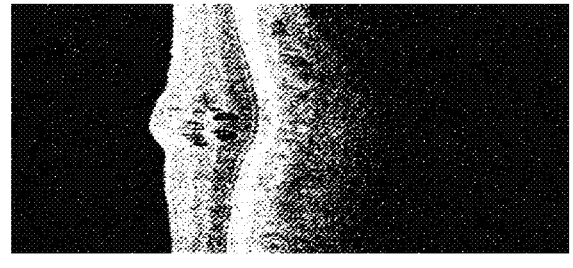

More specifically, to perform labelling for the training set, a raw OCT image or scan (for example as shown in FIG. 4A) is provided to a clinician or clinicians for annotation. In view of one or more characteristics of the image (e.g., brightness, contrast, clusters of similar/dissimilar pixels, etc.), the clinician(s) labels the image to identify regions in the image corresponding to DIRF. FIG. 4E represents a first label that depicts and corresponds with the minimum (high confidence) expected boundary of the DIRF region (minimum DIRF region), reflecting a minimum level of uncertainty regarding the boundary. In other words, the "minimum uncertainty" or "high confidence" label identifies a region of the OCT scan in which the labeler has a high level of confidence (up to and approaching near certainty) that the image includes DIRF. FIG. 1D represents a second label that depicts and corresponds with a maximum (low confidence) expected boundary of the DIRF region (maximum DIRF region) reflecting a maximum or higher level of uncertainty regarding the boundary. In other words, the "maximum uncertainty" or "low confidence" label identifies a region of the OCT scan in which the labeler indicates that the image includes DIRF but has a greater degree of uncertainty regarding the existence of DIRF in those locations. One aspect of the novelty of aspects of the invention described herein is the counterintuitive reliance on degrees of uncertainty as a mechanism to ascertain greater degrees of certainty with respect to fluid location (ground truth). Corresponding disclosures are shown in images A (OCT scans), D (low confidence labels), and E (high confidence labels) of FIGS. 5-11, respectively. As disclosed herein, a maximum DIRF region corresponds to a relatively low level of confidence of a DIRF boundary, whereas a minimum DIRF region corresponds to a relatively higher level of confidence, which may approach near certainty, that the region includes DIRF. As disclosed with respect to the system 10, information including the first and second labels are then introduced into the system, analyzed by one or more AI techniques or neural networks to develop the model for identifying regions of DIRF. These labelled images may be included in the training set. The model is trained to identify the boundary which generally falls between the maximum and minimum DIRF region.

The training set may include additional labelled images. In one example, labelers inspect an image of an OCT scan and label regions of the image as representing the presence or the absence of fluid. In this example, there is a single label per image and only two classes—"fluid" and "background" (or "no fluid"). It is noted that the particular names of the labels are not important. In one example, each image is annotated by only one grader, who labels perceived fluid regions of the image as "fluid", irrespective of the density of the fluid (regions representing both DIRF and FIRF may be annotated as having fluid present) or "no fluid". In another example, each image is annotated by multiple graders.

In another labelling example, discrete soft labels may be annotated on an image. For example, multiple classes are used to correspond to different levels of fluid density. Classes 0, 1, and 2 may be defined to mean no fluid, diffuse fluid, or focal fluid. Classes may be defined to represent image characteristics (e.g., pixel brightness) and/or regions with no fluid, diffuse fluid, and focal fluid, respectively. Classification techniques may include shading, coloring, numerical assignment, or other suitable method. Two, three, four, or more classes may be used if practical. A class weighting may then be assigned to each of the classes, in ascending order of fluid density (in relative units). For example, DIRF may carry a soft-label weight (e.g., 0.5), while FIRF may carry a more definite weighting (e.g., 1.0). Moreover, the classification or class weighting may thereafter convey confidence levels for the level of DIRF at any particular area. For example, a DIRF high confidence classification or label may be used to assess regions similar to the minimum DIRF region and a DIRF low confidence classification or label may be used to assess regions similar to the maximum DIRF region, albeit with additional potential gradations for moderate levels of confidence.

In another labelling example, continuous soft labels are identified in an image. Semantic segmentation networks may be trained to accept a graduated classification of soft labels, where the image characteristic (e.g., pixel brightness) is not assigned entirely to one class or another but rather on a continuum between classes to reflect the labeler's (and/or the system's) uncertainty in the actual class, e.g., associated level of brightness, density, and/or other characteristic. For example, regions of an OCT image can be assigned a label from 1 to 5 where 5 represents the highest level of confidence in the presence of DIRF while 1 represents the lowest level of confidence in the presence of DIRF. Application of such an approach may also be applied to estimate the density of fluid at a per-pixel level. To generate annotated images that identify multiple classes (and therefore labels), labelers annotate the image to produce masks (e.g., set of labels associated with the image, which itself is an image) reflecting the density of fluid at a particular area of the image (e.g., on a per-pixel level) in relative units (e.g., represented by a variety of visual, mathematical, or other type of identifiers). Generating distinguishable annotations may involve the use of specific tooling, e.g., a brush tool, which may increase the intensity of the mask (estimated fluid confidence) as the user clicks and holds using a paint-brush tool.

To enhance labelling, label aggregation may be employed. For example, for labeling strategies that involve multiple labelers annotating the same image for a training set, label aggregation is preferably employed to merge the annotations or labels (e.g., the first and/or second labels) made by multiple labelers or labels of a single OCT scan into a single mask. In one example of label aggregation, the system is configured to calculate or otherwise determine a simple average or weighted average (in the case where continuous labels are used) corresponding to the different annotations available for each image. The model employs the average of the labeled state of each pixel corresponding to the mask generated by the model as the final estimate of the fluid density for that pixel, in relative units. Aggregation techniques improve accuracy over individual masks as the images are averaged over variations in the annotated images and statistically improve accuracy over a greater number of images analyzed.

It is understood that labelling and annotation may vary by labeler depending on labeler training and temporary factors such as images recently labeled by the labeler. The monotonicity assumption provides that the probability of labelling a portion of an image as IRF (e.g., DIRF or FIRF) is proportional to the density of fluid in the region of the macula. For example, it is understood that regions that are more hyporeflective (i.e. low signal intensity in the image) are more likely to be labeled as regions containing IRF compared to a fluid region's usual level of reflectivity in the macula through a monotonic link to the fluid density in that region. For example, the probability that a region is labelled as fluid may be a monotonic function of the fluid density in that region. In other words, as the fluid density increases, the probability of it being labelled increases in kind. Nonetheless, factors can impact the monotonicity assumption. For instance, the likelihood that a pixel or portion of an image labeled as fluid corresponds to fluid may depend on the type of fluid (i.e. DIRF vs. FIRF) in the surrounding pixels. Because DIRF has a lower fluid density than FIRF, the presence of DIRF may be less obvious to the human eye than the presence of FIRF. Small, dense regions may be less likely to be annotated by a labeler than larger, less dense regions due to visibility and visual psychophysical issues. Lower density regions located within higher density regions may be more readily identified. For example, if DIRF occurs between pockets of FIRF, it may be more readily labeled given the relative ease of labeling. Fluid in certain areas of the retina may be more readily identifiable than others due to labelling bias and fluid of equal density may be more apparent to the human eye in certain retinal locations than others. The presence of shadows in the image and/or other artifacts may obscure and/or enhance the appearance of fluid regions, interfering with accurate identification of fluid regions. It is noted that fluid may present as an area of reduced brightness such that the darker the area, the greater potential likelihood of fluid. The presence of large regions of fluid of varying intensity, which labelers are able to identify and annotate, implies that the patient will be treated appropriately regardless of the exact extent of fluid. It is also noted that the scale reflecting pixel darkness (or reduced brightness) may saturate before the point of focal IRF, if every labeler labels fluid below a certain signal intensity.

Once a sufficient number of OCT images are obtained and labeled for the training set, a model is trained to identify the location of fluid including DIRF in an OCT scan and correspondingly in a patient.

As disclosed herein, in some examples, multiple annotations of the images are introduced to the system in order to train the neural network to develop a model. The system evaluates the labels, e.g., each of the first labels and the second labels, compares their respective boundaries as identified by the labels, and generates a fluid confidence map based on the multiple labeled images. The system may also evaluate unlabeled images including retinal scans that display no fluid. This fluid confidence map is outputted in a way that allows the clinician to assess and identify DIRF in a patient's retina. The fluid confidence map may be registered to the original OCT scan image based on underlying characteristics of the image. Regions of FIRF can be identified (by the system or by another technique) and areas of overlap between FIRF and DIRF can be removed according to known techniques. The system may also determine the volume of fluid as shown by the fluid confidence map according to known techniques (e.g., where the volume of FIRF and DIRF are summed and the overlap between them subtracted).

Characteristics of the regions that may be determined by training the system on annotated images include region size, region shape, and region count and location with respect to the fovea. In examples, the characteristics further include an indication of relative density of regions of fluid. Identification and assignment of such characteristics to pixels in the image can be based on classification of individual pixels, as disclosed herein.

FIGS. 4B, 4C, and 4F are outputs (fluid confidence maps) of DIRF (B), FIRF (C), and IRF (FIRF and DIRF) (F), respectively, identified by the trained model for the OCT scan shown in FIG. 4A. Likewise, images B, C, and F of FIGS. 5 through 11 correspond to outputs of DIRF, FIRF, and FIRF and DIRF for each of their respective OCT scans (image A of each respective figure).

Methods for collecting pixelwise regression masks for training is included herein; however, methods for training a pixelwise regression model using only standard semantic segmentation masks, which assign each pixel to a class, is preferred. The methodology utilizes the subjectivity in labelling fluid in macular OCT scans including relative confidence levels to train a pixelwise regression model.

In one example, the system is configured to receive a plurality of images of the macular OCT scans. A group of clinicians labels individual B-scans in a macular OCT cube as described above using semantic segmentation masks such that each pixel is assigned a class probability as discussed above. There exists label disagreement between different labelers on the location of fluid particularly in regions of low certainty and extensive focal change. If multiple labelers grade each image, the images are aggregated to create a set of soft-labelled images. A semantic segmentation network is trained on the annotated image, producing a network whose output at a given pixel is monotonically linked to the density of fluid at that pixel. For example, a semantic segmentation network is trained on the annotated images to assign an identifier to each pixel corresponding to a relative amount of fluid (e.g., a binary determination such as fluid/no fluid; a graduated scaled determination, such as a numerical scale from 0-no fluid, to 10-fluid of a particular density based on confidence levels; and/or more detailed numerical values that represent the level of detail of a particular system or technique). For example, a numerical value (e.g., 0.433, 0.712, etc. on a scale of 0 to 1) may be assigned to reflect a probability of fluid. A transformation is chosen or learned to link the network's probabilistic output to a measurement which is correlated (e.g., linearly proportional) to the true location of the fluid. The determination of whether a pixel represents fluid or no fluid is provided by thresholding the network's output. The relative density of fluid is determined by transforming the network's output using a monotonic link function. For example, the likelihood of labelling a particular pixel as fluid is proportional to the density of fluid at that pixel and the process of training the system produces an identification model, application of which provides an output corresponding to the density of fluid at that pixel based on the relative brightness of the pixel in combination with the labelled images of the training set. The resulting model produces an output mask for individual B-scans that identifies the location of fluid throughout the macula in relative units of confidence. The model may also be used to label DIRF and FIRF categorically by learning a thresholding function over the fluid confidence output.

In addition to what has already been discussed, there are several methods that can be used to train the system including AI and develop a model that can identify areas of fluid in an OCT scan or macular OCT cube.

In one example, based on the model(s) developed through system training (e.g., generating threshold brightness values, developing class identifiers for each pixel, etc.), a program can be provided to measure or otherwise identify the density of fluid throughout the macula (based on an image of an OCT scan). AI (e.g., machine learning) techniques are applied to generate a model to analyze images (retinal scans) and generate data for presentation (regions of DIRF). The system may also be trained and retrained through relearning of analysis errors, e.g., where, in training, the system has identified "no fluid" areas as containing fluid, the system may be introduced to new images for training purposes.

One method of training the system is individual segmentation mask training. In this method, a relative fluid density detector model involves no label aggregation and applies to a labelling strategy where labels are identified as fluid or no fluid. This methodology assumes that a labeler is more likely to label regions of fluid (and relative fluid density of those regions) on the image in proportion to its density. Labeled images are used to train a U-Net semantic segmentation network without any aggregation of images that have been labeled multiple times. Therefore the network learns, over a large set of images and annotations, the probability that a given pixel would be labeled as either fluid (e.g., DIRF) or not based on an estimated measurement of the fluid density at that pixel (e.g., based on the brightness or intensity of the pixel in the image and/or other image characteristics). Since the probability of a pixel being labeled as fluid is monotonically linked with the density of fluid in the region of the eye represented by that pixel, the network employs a model that identifies a pixel as having a particular degree of fluid density. Based on the identification, the model assigns a class label to that pixel, and generates an output corresponding to the fluid density at each pixel.

Another training methodology is training on aggregated labels. In this example, the system trains a U-Net semantic segmentation network by creating or using existing soft labels. When a labelling strategy is employed using multiple labelers, an aggregation method averaging labels for all available annotations for the same image is used to create a map of approximate probability as to how a pixel would have been labeled by a random labeler.

Training a semantic segmentation network with one or more annotated images of an OCT scan minimizes the pixelwise cross-entropy between the ground truth class distributions (i.e. the actual density of fluid within the patient's eye) and the model's predicted class distribution (i.e. based on evaluation of an image and identification and assignment of pixels therein). Therefore the system learns to create maps that provide an estimated probability that a given pixel belongs to a particular class, which by assumption are monotonically linked to the density of fluid in the retina.

For labelling strategies relying on discrete soft labels, class weights or probability-based labels are used to exaggerate the monotonic link between fluid volume, location, relationship with FIRF and labelling probability. The network learns a labelling probability map based on a weighting function applied to pixels in the image in view of the labels, the classes of each fluid confidence map being monotonically linked to the likelihood of fluid in the patient's eye. This method may further employ label dropout, which involves dropping out pixel classes (i.e. labels) randomly with probability proportional to the class weight in the aggregated mask, and setting the non-dropped out pixels to have class probability 1.

Another training methodology is pixelwise regression, which may apply to most labelling strategies. The loss that is optimized is not the cross entropy loss but a pixelwise regression loss. See Yao, Wei, et al. "Pixel-wise regression using U-Net and its application on pansharpening." Neurocomputing 312 (2018): 364-371.

The network is trained to assess the extent of DIRF in terms of volume, location, and relationship with FIRF. For example, while the segmentation networks learn to assess fluid density in relative units, the system can learn the monotonic link function between the network's output and the likely fluid density. Network output may be passed through a monotonic function that converts it to a fluid density measurement. In one example, a ground-truth dataset containing an aggregated evaluation metric, such as overall fluid volume or ordering of scans by degree of fluid density, can be used to induce a link function that warps the network's relative-scale estimates of the fluid density into a true scale. This involves selecting a family of functions to map the network's output to a fluid density estimate. On a large dataset, the parameters of the function are estimated so that an aggregation function of the fluid is optimized with respect to some ground truth. The parameters of the transformation function can be learned using gradient descent in cases where the link function is differentiable or by non-differentiable optimization methods such particle swarm optimization in the cases where it is not. Assuming sufficient variation in the presentation of fluid regions in the image, the output from the system employing the learned transformation functions would be expected to correspond linearly to the true fluid volume in the patient's eye; however, output (such as classification of pixels) generated from employment of this method would be provided in relative terms, lacking absolute units.

There are several function families that can be used to learn the link function. A polynomial regression from the network's output (between zero and one) to estimate the fluid density can be used. In some examples, the model can be constrained to be monotonic. A monotonic neural network can also be used. Other methods of monotonic regression may also be applicable as would be known to a person of ordinary skill in the art. See, e.g., Hawkins, "Fitting monotonic polynomials to data." Computational Statistics 9.3 (1994): 233; Sill, "Monotonic networks." Advances in neural information processing systems (1998); McKay et al, "A variable selection approach to monotonic regression with Bernstein polynomials." Journal of Applied Statistics, 38.5 (2011): 961-976.)

As the probability of labelling a region of fluid may saturate before the point of FIRF, a true bijective link function may not exist. However, these effects would occur only at the upper edge of the distribution of fluid density (e.g., between DIRF and FIRF) and would therefore not be expected to be clinically significant.

Properties of the detected regions of pathology, including volume, size, signal characteristics and location, as well as changes from previous scans, are extracted from the mapped images. The extracted features are then used to make determinations and predictions about the patient's retina disease progression and optimal treatment choices.

The network may be trained to take information in adjacent B-scan slices into account by either injecting the adjacent scans as extra channels in the input or by using 3d convolutions in a U-Net style architecture. The segmentation of focal pathologies returned by the U-Net may be made more accurate by filtering the continuous regions in the network's output using a random forest classifier. This classifier takes into account features of the segmented regions such as its size, smoothness, and location. The random forest classifier is trained to determine whether segmented regions represent real focal pathology or whether they are false positives, using the output of the trained segmentation network and the ground truth annotations as training data. When the random forest classifier predicts that a segmented region is a false positive with a certain level confidence (chosen by cross-validation), that region is eliminated from the segmentation output.

In the step of focal region detection, there is an abundance of unlabeled data that may be used to improve performance on the task. In this example, rather than a semi-supervised learning approach, the system 10 may use a pre-training step on a U-Net segmentation network to make use of the unlabeled data. The U-Net is pre-trained to solve an auto-encoding problem on unlabeled data, progressively removing the skip connections in order to force the network to transmit information about retinal structure through the deeper layers of the network.

In a U-Net segmentation network that has been trained to recognize the focal region of, say, FIRF in a supervised learning setting, the deeper layers of the network are expected to encode information about the global structure of the B-scan being segmented or examined. Therefore this form of pre-training used in the system 10 should give the network an advantage in solving the supervised problem by inducing the encoder network to create an embedding space with useful features without using the supervised training data. Simply pre-training U-Net on unlabeled data with the usual architecture would not be effective, however, since the skip connections between the first and final layers of the network would allow the input image to be copied directly to the output layer of the network, solving the problem without inducing any useful representations in the deeper layers of the network. Therefore, the system 10 may progressively remove the skip connections in the network architecture, so that representations must be created and transmitted through the deeper layers of the network. Initially the first skip connection may be removed, and once the network has learnt the auto-encoding task in that configuration, the next skip connection is removed, and so on. Using this mechanism, the more abstract layers could learn about typical structures in retinal OCT B-scans, which are then in place during the supervised learning process. This will improve the model performance that results from a given amount of supervised training data.

The models used in the system 10 create predictions at each stage of fluid detection or other stages that provide contextual information such as fovea finding. In all cases there is uncertainty associated with the model's output. This uncertainty is quantified and may be visualized to provide doctors and users with information about how confident the model is in its predictions. Feedback about model uncertainty may be presented in the form of, e.g., heat-maps that are weighted by the model's confidence and summary signals (red/yellow/green) that aggregate model uncertainty in each of the stages of the data processing pipeline.

Having trained the model to analyze images and generate an output (such fluid confidence map corresponding to pixels of various classes), the output can be further manipulated and/or presented in a variety of ways. For example, rather than analyzing probable fluid density, the model may assign pixels to a set of classes corresponding to different fluid densities. Any of the fluid density measurement methods can also be adapted using a thresholding technique to find predicted regions of DIRF (and, in some examples, FIRF). As disclosed herein, DIRF is defined as the presence of fluid but at a lower density than that of FIRF, which is saturated. Therefore, some threshold of fluid density which separates DIRF and FIRF, with the addition of likely anatomical constraints on the distribution of fluid and its propensity to collecting as DIRF or FIRF. Since the segmentation network's class probability output is monotonic with respect to the fluid density, thresholds can be set to infer the categories of focal and diffuse IRF. For example, the network may produce a numerical output for each pixel, which can be compared relative to a numerically established threshold for DIRF and/or FIRF.

The optimal threshold for separating regions of FIRF from regions of DIRF can be learned from the training data. In some examples, the threshold value, which indicates an interface between the two regions, can be mapped to the image and presented to the clinician. Due to relative density and relative brightness in an image, FIRF is easier to label and thus inter-labeler agreement is more likely when labelers are asked to annotate FIRF only and not DIRF. Therefore, the threshold can be set to maximize the IoU or average cross-entropy between the network's predicted FIRF regions and a ground-truth dataset of FIRF only. As an example, FIRF can be identified reliably, and regions of overlap removed or otherwise identified. The ground-truth dataset can be validated by testing inter-rater agreement between multiple graders, and the optimization can be performed against soft ground-truth labels created through an aggregation process over multiple ground-truth labels from different graders.

To maximize performance of the classification and/or mapping steps, a range of standard and/or non-standard image pre-processing techniques may be applied including: axial motion correction; flattening of the retina; normalizing regions of high contrast; artefact recognition including shadowing; blink artefact correction; and 3D smoothing to reduce the effects of speckle.

Additional information relating to various methodologies for model training are described in Australian Application No. Australian Application No. 2018903511, which is hereby incorporated by reference.

Once the system is trained, the system (e.g., a neural network or other machine learning technique) can identify and/or estimate a location and/or size of a DIRF region based on the model generated from the training set. The model can then be validated or otherwise evaluated to ensure an overall level of confidence and consistency for the output.

To validate or evaluate the system training, the system or method may include a method or step to evaluate the system's performance in measuring the distribution of fluid throughout the retina. For example, a fluid confidence map is output based on pixel classification by application of the model. The fluid confidence map can be compared with an average confidence map generated by analysis of multiple annotated images from multiple labelers. In this manner, the average is assumed to correspond to a "best guess" of the fluid density of the patient's eye, and closer to the histological ground truth than a single annotated image. In another example, aggregation methods can be coupled with rank correlations of the images. Labelers can also provide annotations corresponding to the overall fluid quantity based on the image data. Based on a comparison of the fluid confidence map of an image and the image annotated to present the overall fluid quantity, a rank correlation can be calculated between total fluid volume calculated from the system's output and the ground truth labels based on the averages of the annotated images. Labelers can further identify the fluid quality in a ranked way, compare pairs of images and state which ones are more or less accurate, create an ordering for the images in terms of fluid quantity, and compute the rank correlation with the fluid confidence maps output based on the model.

Additionally or alternatively, the output can be evaluated with regard to significance in facilitating clinical decision-making (e.g., are clinical outcomes improved, compromised, etc.). Thus, the system may be evaluated in the context of clinical decision-making such that total fluid volume is taken as an input.

In some examples, the clinical decisions are compared to the decisions made by experts without the aid of the fluid confidence map. If the level of agreement between the fluid confidence map and the experts is similar to the level of agreement among the experts themselves, then the model output has achieved a "best guess" map in accordance with the images upon which the model is developed.

It is noted that, in some examples, data corresponding to the FIRF region may be obtained. For instance, the system can be trained to analyze images and identify the FIRF region. In other examples, the FIRF region can be identified by other systems and/or suitable techniques, the corresponding data provided to the system for analysis. Having obtained data regarding the DIRF and/or FIRF regions, the system may generate and/or output an image that shows the location of the DIRF region and/or a combination of the DIRF region and the FIRF region.

After a system is trained and preferably validated to identify regions of DIRF, the system may be used to analyze OCT scans obtained from a patient that have not been annotated by a clinician in a method of treating a patient for macular disease. In such a method, one or more images of an OCT retinal scan is obtained. Applying the model developed through the training set to the image, the system analyzes the image characteristics in view of the model to identify the fluid regions including DIRF. For example, the model identifies one or more pixels of the image as corresponding to the DIRF region. Based on the identified pixels, the system generates an estimated DIRF region and outputs an image with the estimated DIRF region registered on the image. In examples, a FIRF region can be identified by the system and/or data associated with the FIRF region is received by the system and applied to the image. For instance, a total region of fluid will correspond to both the DIRF and FIRF regions. Any areas of overlap between the two may be eliminated, leaving regions of DIRF for presentation. In some examples, the generated image can be displayed with identifiers for the DIRF and the FIRF regions (i.e. different colors, relative levels of brightness, overlays, etc.).

As an example, an OCT scan obtained from a patient in the form of FIG. 4A (which would in this example not be a scan from the training set) would be inputted into the system and an output in the form of FIG. 4F, which would depict the IRF (both the FIRF and DIRF), would be produced by the system. Alternatively or additionally, the system may output the location of DIRF, for example, in the form of FIG. 4B or FIRF in the form of FIG. 4C. The output images facilitate the method of treatment by the clinician.

In some examples, an estimated DIRF region is registered on each of multiple images of the OCT scan, such that when combined in order, the system can generate an estimated volume of IRF and more specifically, DIRF (e.g., within the macular cube). The estimated DIRF volume may be viewed from different perspectives via computer manipulation of the volumetric image to assist with the clinical decision making process.

It is noted that a patient's retinal OCT scans are typically acquired by an OCT scanner (e.g., 18), which may be in the doctor's clinic, a hospital, a public place or even in the patient's home, and the images of the OCT scans are analyzed as per the above method. Alternatively, the OCT scans may be transmitted securely to the cloud, and then analyzed. The OCT scanner and other components of the system may be therefore be remote or near each other.

The method and system may include pre-processing the image and the subsequent image of the retina to normalize for systematic differences in the images produced by the different OCT scans. Particularly, the method further includes transforming the image and the subsequent image of the retina to normalize parameters of the image and the subsequent image. These parameters include, for instance, contrast and scaling such as pixel-by-pixel analysis.

The method and system may further include registering the image and the subsequent image of the retina into a standard coordinate space. The method and system may further include aligning the subsequent image into the standard coordinate space using a fundus image of blood vessels of the retina received from the OCT scanner. Alternatively, or additionally, the method and system may further include classifying, using a fovea finding classifier, each of the pixels of the image into fovea and retina classifications; and identifying the center of the fovea of the retina in the image based on results of the fovea and retina classifications of the pixels. The image and the subsequent image are then aligned into the standard coordinate space using the center of the fovea.

The first step of the classification involves classifying B-scans according to whether the center of the fovea is contained within the B-scan or not. For this purpose, a neural network classifier is trained to predict a binary output variable that indicates whether a B-scan contains the center of the fovea. The network takes as input a series of consecutive B-scans that may or may not have been pre-segmented using a layer segmentation model, and the target variable indicates whether the central scan in the slice contains the center of the fovea. The network used in this step is a typical convolutional neural network with either 2D or 3D convolutions followed by a fully-connected layer which calculates a single output variable. This classifier may be trained on the raw B-scans captured by the OCT scanner 18, or it may be trained on images segmented by the layer segmentation system described below. The second stage involves finding the location of the fovea center in the selected B-scan. This can be accomplished by a regression network (CNN followed by FC layer) that outputs the location of the fovea center relative to the width of the B-scan. The training data for fovea finding may be collected by marking the center of the fovea on a reconstructed fundus image. Foveal finding may also be accomplished by using a regression network like the one described for the second stage on reconstructed fundus images.

When an OCT scan contains severe disease, the fovea may be hard to locate using B-scans only. In this case, image registration on past scans may be used to infer the location of the fovea in the diseased scan. Another approach is to fit a parametric model (e.g. penalized B-spline surface) to the retinal boundaries of one diseased and one healthy eye (if available), and then align the surfaces in the healthy regions only, thus registering the diseased eye to a reflected image of the healthy one, allowing the location of the fovea to be inferred from the healthy eye.

Once the system provides an output or outputs, the clinician may proceed with treatment of a patient. An aspect of the present system and method includes a system for incorporating individual practitioner preferences for several variables in the protocol, including interval increments, order of choice of drugs and protocol choice for different drugs.

An assessment of the retina may include the diagnosis of a disease such as macular degeneration, diabetic retinopathy and retinal vein occlusion. The progress assessment may include an assessment on the progress of one of these diseases following a treatment protocol being applied to the retina of the patient. Historically, for example, treatment protocols that were used for intravitreal injections of anti-VEGF agents were very simple, consisting of monthly injections. Subsequently, agents have been introduced for which the frequency of injection has been lower, but the duration of effects of the drug, assessed using OCT scans, can be variable. That is, some eyes require injections every four weeks, but others require injections once every 12 weeks or more. Optimally, the treatment of exudative macular disease is individualized for the patient such that the least number of injections results in the greatest long-term vision and least macular edema. That is, the choice of drug, dose and interval between treatments is tailored to the individual eye. These decisions are currently made by ophthalmologists using information from measurements of patients' vision, changes in symptomatology and, most importantly, visual inspection of OCT images. OCT scans are not only more objective, but also more sensitive to change than the vision measurements and reported vision. The treating ophthalmologist generally assesses the OCT scans for the presence or absence of fluid, changes in comparison with previous scans and the rates of any changes.

The detection, characterization and quantification of DIRF is particularly significant when assessing the therapeutic effect of a treatment protocol. That is, as DIRF develops before FIRF and may be last to disappear, it is a sensitive parameter for determining the onset and diminution of therapeutic effect of therapeutic agents. The present invention assists the clinician in determining the location of pathology in the form of DIRF, as well as FIRF. An indication of the volume of the DIRF is determined and the method derives the assessment of the retina based on the DIRF and its volume. In other examples, the size, shape, contour, and count of the DIRF is considered by the method.

In respect of the above method, the progress assessment of the retina can be used to determine the efficacy of a treatment protocol. That is, the method may assess a patient's OCT scans of their retina throughout their treatment period by comparison of the multiple patient scans over time, and these may be used to recommend a drug, treatment interval, potential additional tests required, potential visual outcome in the long-term, etc.

For example, images of the retina are analyzed according to the present invention and are used to derive the assessment of the retina. As mentioned, a comparison of the most recent assessment (OCT scan output) with a previous one is performed. In the case of OCT scans acquired in the clinic or the doctors' office, this may be once a month or less frequently, governed by the frequency of attendance of the patient. In the case of the OCT scanners in the community or in the patient's home, scans may be acquired more frequently. In any event, the resultant progress assessment may be used by a clinician to inform the following decisions: whether an injection should be given and when; which drug should be injected; when the next injection be performed; which drug should be injected at the next injection; whether further tests are required; whether different diagnoses should be entertained; whether any other problems need to be addressed, potentially through examination and review by the doctor; if OCT scans are to be acquired in between visits to the doctor (injections), then further questions may arise; the nature and extent of therapeutic effect of the most recent injection; whether the rate of change of OCT parameters is indicative of future response to the same drug; whether the rate of change of OCT parameters is indicative of future response to another drug; what is the likely long-term and short-term visual outcome with the current drug; whether the patient should have any change in their management prior to the next planned visits; the likelihood of other macular disease (geographic atrophy, for example) occurring; the likely visual acuity at various stages in the patient's management; how many injections is the patient is likely to require in the future and how often; and whether and when the condition is likely to recur if the patient stops injections, is the condition is likely to recur.

Further, the system and method may provide a comparison of the present assessment may also be compared with previous assessments throughout the patient's visits and there may be a regular comparison with the initial assessment if the patient's condition worsens. There is also a comparison with the assessment and possibly the OCT scans from times when the patient was on a different drug and different injection frequency (interval). The treatment protocol also takes into account patients returning earlier than planned for injections and also later than planned. In addition, flexibility exists around patient choice and doctor choice with respect to performing both injections at the same time, even separating the two etc. is incorporated into the protocol such that the protocol differs from published ones in which real world evidence and experience is not incorporated.

In order to assess disease progression in scans from the same patient collected across time, successive images may be aligned in a common coordinate system. For this purpose, the system 10 may use a fundus image of blood vessels of the retina received from the OCT scanner as the blood vessels have fixed locations in the standard coordinate space. That is, the blood vessels locations are registered based on a reconstructed fundus image. Fovea-finding may be incorporated into this space. The alignment may be performed in Euclidean or spherical coordinate space.

In one example, the system 10 outputs an assessment which may be one of a selection of optimal treatment regimens for individual patients based on the features of their OCT scan and treatment history. To this end, the patient's treatment history and the features extracted in the previous stage to train machine learning models are used to predict the outcomes of treatment regimes for patients. These models may include classical machine learning models such as decision trees, as well as neural network methods that can respond to the variable-length nature of a patient's treatment history such as RNNs. The models take into account features of the entire treatment history such as: time between treatments; features of disease at each time point; past treatments used; past treatment regimens (protocols) used; treatment history in the other eye, etc.

The training framework for the models either takes the form of a supervised learning problem (predict the outcome for the patient given this treatment history), or as an off-policy reinforcement learning problem, where the model learns a value function that estimates the usefulness of each treatment option in a given scenario.

In both cases, the goal is to estimate the causal effect of a treatment option, so that the optimal treatment can be chosen. To do this, any potential confounders (attributes of the patient that the doctor considers when prescribing treatment) will be identified, measured, and added to the patient history for the models to take into account. This way, a propensity score adjustment can be made and the causal effect of treatment can be estimated. Then, the optimal treatment can be selected by optimizing the predicted effect of each treatment option.

The feature extraction component of the system 10 will enable the construction of inferential models in a low data scenario. However, once the system 10 is deployed, more patient treatment time-series will be collected. Once sufficient data becomes available, the system 10 may further include a representation learning approach to the time-series prediction problem outlined above. This will involve training deep neural networks end-to-end in the reinforcement learning setting to perform feature extraction on the raw OCT data such that the learned features have predictive value for the patients' future health outcomes. These networks will be multi-modal in that they will also take into account inputs such as patient demographics and treatment history. This approach has the potential to learn new features of OCT images that are clinically relevant, but are not known in a rule-based feature extraction system.

Those skilled in the art will also appreciate that the invention described herein is susceptible to variations and modifications other than those specifically described. It is to be understood that the invention includes all such variations and modifications.

The invention claimed is:

1. A system for analyzing images of a retina captured by an optical coherence tomography (OCT) scanner, the system comprising:
   at least one OCT image of a retina obtained from a patient;
   a memory comprising a trained model configured to determine a location of diffuse intraretinal fluid in the patient retina based upon the at least one OCT image wherein the trained model is configured to determine the location of diffuse intraretinal fluid based on different OCT images in a training set and
   wherein the different OCT images of the training set comprise a plurality of images that each comprise at least two labels within a region of diffuse intraretinal fluid and wherein the at least two labels distinguish between high confidence location of diffuse intraretinal fluid and low confidence location of diffuse intraretinal fluid within the region of the diffuse intraretinal fluid; and
   a display that outputs a fluid confidence map that reflects the location of the diffuse intraretinal fluid in the patient retina within the at least one OCT image based on the trained model.

2. The system of claim 1 wherein the model is trained via machine learning.

3. The system of claim 1 wherein the system further includes an optical coherence tomography scanner configured to acquire OCT images.

4. The system of claim 1 wherein the model is further configured to determine the volume of retinal fluid in and the display outputs the volume of the fluid.

5. The system of claim 1 wherein the trained model is further configured to determine the location of focal intraretinal fluid (FIRF) in the retina.

6. A method of analyzing images of a retina captured by an optical coherence tomography (OCT) scanner, wherein the method includes the steps of:

receiving an image of a retina of a patient captured by an OCT scanner;

determining a location of diffuse intraretinal fluid in the patient image using a trained model, wherein the trained model is configured to analyze the location of diffuse intraretinal fluid on an OCT scan based on different OCT images in a training set including a plurality of OCT images each having at least one label indicating a high confidence location of diffuse intraretinal fluid within a region of diffuse intraretinal fluid and at least one label indicating a low confidence location of diffuse intraretinal fluid within the region of the diffuse intraretinal fluid; and outputting an image with a fluid confidence map that reflects a predicted location of the diffuse intraretinal fluid in the patient image based on the trained model.

7. A system for analyzing images of a retina, wherein the system comprises:

an Optical Coherence Tomography (OCT) scanner configured to capture images of a retina of a patient, each of the images having a plurality of pixels;

a memory comprising a series of instructions in the form of a trained model that is configured to analyze the location of diffuse intraretinal fluid on images received from the OCT scanner based on probability-based labels relating to the level of diffuse intraretinal fluid in a training set, wherein the training set comprises a plurality of images that each comprise at least two labels within a first region of diffuse intraretinal fluid, and wherein the at least two labels distinguish between high confidence location of diffuse intraretinal fluid and low confidence location of diffuse intraretinal fluid within the first region of the diffuse intraretinal fluid;

a processor in data communication with the OCT scanner and the memory that is configured to implement the series of instructions that include receiving an image of a retina of a patient captured by the OCT scanner, determining regions of diffuse intraretinal fluid in the patient image including by assessing the relative probabilities of diffuse intraretinal fluid at a given location, and analyzing the diffuse intraretinal fluid region or regions of pathology to derive an assessment of the retina of the patient; and a display for outputting a fluid confidence map that reflects the location of the diffuse intraretinal fluid in the diffuse intraretinal fluid region of the patient image as determined by the trained model.

* * * * *